(12) United States Patent
Hunt

(10) Patent No.: US 10,543,331 B2
(45) Date of Patent: Jan. 28, 2020

(54) FLUID DELIVERY SYSTEM TO AIRWAY

(71) Applicant: Cook Medical Technologies LLC, Bloomington, IN (US)

(72) Inventor: James B. Hunt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 377 days.

(21) Appl. No.: 15/362,976

(22) Filed: Nov. 29, 2016

(65) Prior Publication Data

US 2017/0151404 A1    Jun. 1, 2017

Related U.S. Application Data

(60) Provisional application No. 62/261,450, filed on Dec. 1, 2015.

(51) Int. Cl.
*A61M 16/04* (2006.01)
*A61J 15/00* (2006.01)
(Continued)

(52) U.S. Cl.
CPC ........ *A61M 16/049* (2014.02); *A61J 15/0011* (2013.01); *A61M 16/01* (2013.01);
(Continued)

(58) Field of Classification Search
CPC ............ A61M 16/049; A61M 16/0493; A61M 16/0497; A61M 19/00; A61M 25/00;
(Continued)

(56) References Cited

U.S. PATENT DOCUMENTS 3,049,806 A * 8/1962 Cofresi ................ A61C 17/043
                                                              433/93
4,167,814 A    9/1979 Schubert
(Continued)

FOREIGN PATENT DOCUMENTS

WO    WO 2004/089271 A2    10/2004
WO    WO 2014/089519 A1    6/2014

OTHER PUBLICATIONS

Extended European Search for related EPO application No. 16201504.4-1664; dated Mar. 30, 2017 (9 pgs).
(Continued)

*Primary Examiner* — Rebecca E Eisenberg
*Assistant Examiner* — Dung T Ulsh
(74) *Attorney, Agent, or Firm* — Brinks Gilson & Lione

(57) ABSTRACT

A fluid delivery system is provided including an elongated member with a lumen, a first portion, a second portion, and a third portion, wherein the second portion is disposed between the first portion and the third portion. The elongated member is insertable into a patient's mouth such that the second portion is disposed entirely within the patient's mouth while the first portion and third portion extend from a point inside the patient's mouth to a point external the patient's mouth. The fluid delivery system also includes a locking system slidably engaged with the elongated member, the locking system removably engageable with the patient's teeth. Further, the second portion is configured to allow drainage of a fluid from within the lumen to a point external the elongated member.

12 Claims, 6 Drawing Sheets

(51) Int. Cl.
*A61M 16/01* (2006.01)
*A61M 39/10* (2006.01)
*A61M 19/00* (2006.01)
*A61M 31/00* (2006.01)
*A61M 25/00* (2006.01)
*A61M 25/02* (2006.01)

(52) U.S. Cl.
CPC .... *A61M 16/0463* (2013.01); *A61M 16/0488* (2013.01); *A61M 19/00* (2013.01); *A61M 25/00* (2013.01); *A61M 31/00* (2013.01); *A61M 39/10* (2013.01); *A61M 2025/022* (2013.01); *A61M 2205/3334* (2013.01); *A61M 2209/088* (2013.01); *A61M 2210/0625* (2013.01); *A61M 2210/0637* (2013.01)

(58) Field of Classification Search
CPC .......... A61M 31/00; A61M 2025/0003; A61M 2025/00; A61M 2025/0009; A61M 2025/0019; A61M 2025/0031; A61M 2025/00; A61J 15/011; A61H 13/00; A61H 13/005
See application file for complete search history.

(56) References Cited

U.S. PATENT DOCUMENTS

| | | | | |
|---|---|---|---|---|
| 4,425,911 | A | * | 1/1984 | Luomanen ........ A61M 16/0488 128/200.26 |
| 8,540,660 | B2 | * | 9/2013 | Martin .............. A61M 16/0006 604/24 |
| 2003/0054317 | A1 | * | 3/2003 | Burney .................. A61C 17/08 433/96 |
| 2010/0016908 | A1 | | 1/2010 | Martin et al. |
| 2011/0220124 | A1 | * | 9/2011 | Vaska ...................... A61F 5/566 128/848 |
| 2012/0199135 | A1 | * | 8/2012 | Podmore ................ A61F 5/566 128/848 |
| 2013/0203012 | A1 | | 8/2013 | Walker |

OTHER PUBLICATIONS

Response filed Dec. 6, 2017 for EP16201504.4, 21 pgs.
Communication Under Rule 71(3) EPC Intention to Grant for EP16201504.4 dated Mar. 13, 2018, 33 pgs.

* cited by examiner

FLUID DELIVERY SYSTEM TO AIRWAY

CROSS-REFERENCE TO RELATED APPLICATIONS

The present patent document claims the benefit of the filing date under 35 U.S.C. § 119(e) of Provisional U.S. Patent Application Ser. No. 62/261,450 filed Dec. 1, 2015, which is hereby incorporated by reference.

FIELD

The present disclosure relates generally to medical devices and more particularly to a fluid delivery system to an airway of a patient.

BACKGROUND

The statements in this section merely provide background information related to the present disclosure and may not constitute prior art.

An endotracheal tube (ETT) is a medical device used to establish and maintain an airway to the patient's lungs. Ventilators are frequently connected to ETTs to assist a patient who is having difficulty breathing independently. Endotracheal tubes are generally long, tubular devices with at least one lumen that may be inserted through a patient's mouth and down into the patient's trachea.

While ETTs are generally used as a temporary solution for a patient that requires assistance breathing, they still may remain in a patient for days, or even weeks, at a time. ETTs are generally considered uncomfortable and even painful for patients, which can be exacerbated by prolonged and continuous use. A patient's gag reflex may also cause problems, especially during the initial insertion of the ETT into the patient's trachea.

Physicians have used local anesthetic spray or sometimes even nerve blocks injected into the nearby tracheal tissue to help alleviate the discomfort or pain. These methods are often used prior to the initial insertion of the ETT into the patient's trachea. However, these solutions are only temporary, and repeat injections are often required to maintain their effectiveness. Thus, there exists a need for a device and method that provides continuous relief from the pain and discomfort of an indwelled ETT throughout the entire lifespan (or a significant portion) of the ETT.

SUMMARY

In one form of the present disclosure a fluid delivery system is provided. The fluid delivery system comprises an elongated member comprising a lumen, the elongated member comprising a first portion, a second portion, and a third portion, wherein the second portion is disposed between the first portion and the third portion, wherein the elongated member is insertable into a patient's mouth such that the second portion is disposed entirely within the patient's mouth while the first portion and third portion extend from a point inside the patient's mouth to a point external the patient's mouth. The fluid delivery system further comprises a locking system slidably engaged with the elongated member, the locking system removably engageable with the patient's teeth. Further, the second portion of the elongated member is configured to allow drainage of a fluid from within the lumen to a point external the elongated member.

The fluid delivery may also include the locking system comprising a first block and a second block, the first block removably engageable with a front of the patient's teeth and the second block removably engageable with a back of the patient's teeth. The fluid delivery system may further include the first and second blocks being slidable along the first and third portions of the elongated member, wherein the first and second blocks are lockable to prevent sliding along the first and third portions of the elongated member. The fluid delivery system may also include the second portion comprising at least one port that allows drainage of a fluid from within the lumen to a point external the elongated member. The fluid delivery system may further comprise a permeable membrane secured to an external surface of the second portion of the elongated member. The fluid delivery system may also comprise an opening through which a tracheal tube can be inserted.

In still another form of the present disclosure, a method of delivering a fluid is provided. The method comprises providing a fluid delivery system that comprises an elongated member comprising a lumen, the elongated member comprising a first portion, a second portion, and a third portion, the fluid delivery system further comprising a locking system slidably engaged with the elongated member, wherein the second portion of the fluid delivery system is configured to allow drainage of a fluid from within the lumen to a point external the elongated member. The method also comprises inserting the fluid delivery system into a patient's mouth such that the second portion is disposed entirely within the patient's mouth and the first and third portions extend at least partially into the patient's mouth. Further, the method comprises engaging the locking system with the patient's teeth. The method also comprises supplying a fluid through the lumen of the fluid delivery system such that the fluid flows out of a portion of the lumen disposed within the second portion of the elongated member and into the patient's body.

The method may also include the locking system comprising a first block and a second block, wherein the first block is engageable with a front side of the patient's teeth and the second block is engageable with a back side of the patient's teeth. Further, the step of engaging the locking system with the patient's teeth may further comprise sliding the first block along the elongated member until it is adjacent to the front side of the patient's teeth, locking the first block to the elongated member so as to prevent movement of the first block with respect to the elongated member, sliding the second block along the elongated member until it is adjacent to the back side of the patient's teeth, and locking the first block to the elongated member so as to prevent movement of the first block with respect to the elongated member. The method may also comprise inserting a tracheal tube through an opening in the fluid delivery system and into the patient's trachea.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
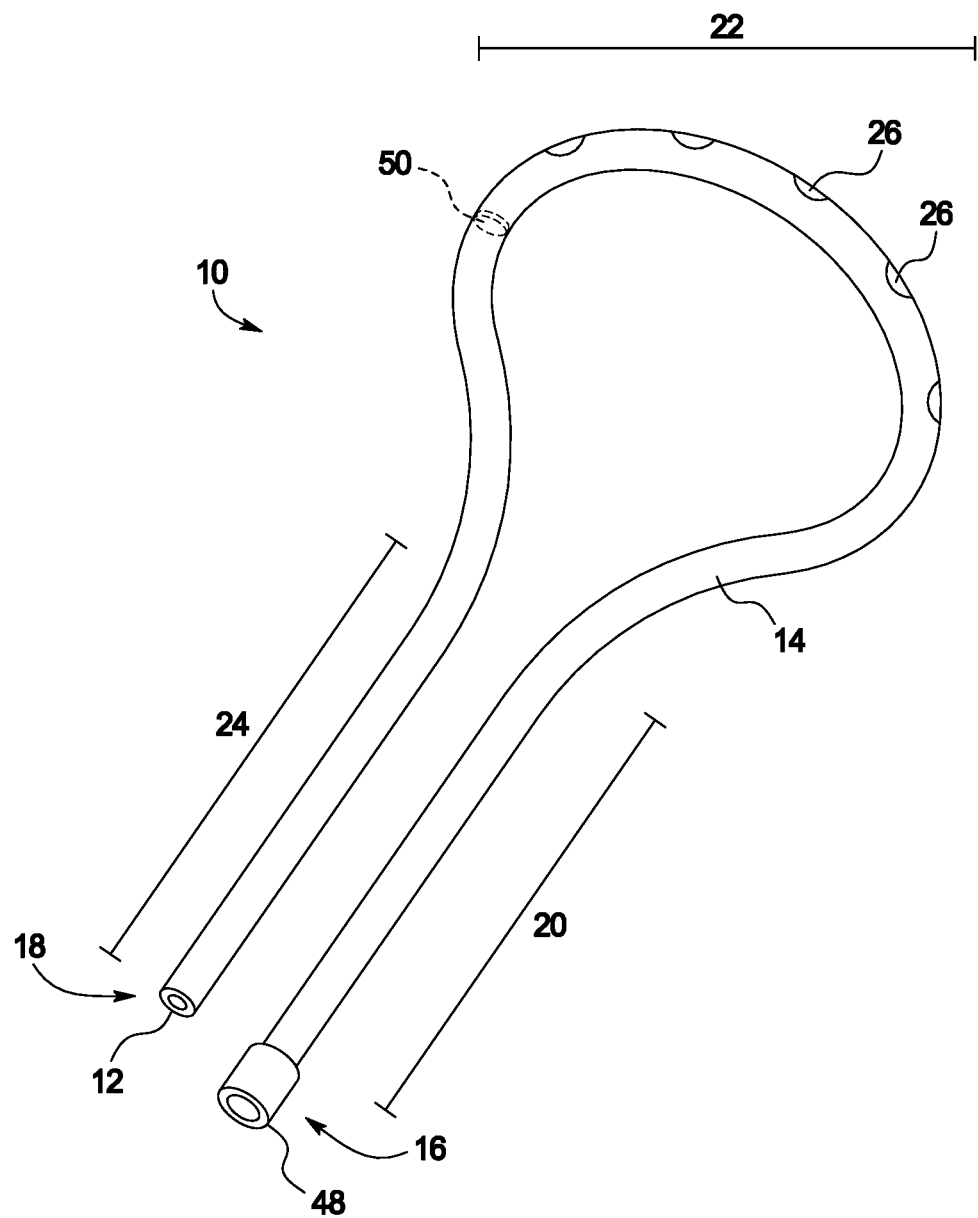
FIG. 1 is a view of a fluid delivery system in accordance with an embodiment of the invention.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

The terms "proximal" and "distal" are used herein in the common usage sense where they refer respectively to a handle/doctor-end of a device or related object and a tool/patient-end of a device or related object.

Referring to FIG. 1, a fluid delivery system 10 is shown. The fluid delivery system 10 may include an elongated member 14 with a lumen 12 that extends along a portion of or the entire length of the elongated member 14. The elongated member 14 may also include a first end 16 and a second end 18. The elongated member 14 may include a first portion 20, a central, or second, portion 22, and a third portion 24. The first and third portions 20, 24 may be generally or substantially straight along their axial lengths and run substantially parallel to each other such that the first and second ends 16, 18 are positioned near each other. The central portion 22 may have a looped, or arced, shape. The lumen 12 may extend from the first end 16, through the first portion 20, through the central portion 22, through the third portion 24, and to the second end 18. Alternatively, the lumen 12 may not extend completely through the entire length of the elongated member 14, and instead may only extend partially through the elongated member 14. The central portion 22 may include one or more ports 26 that provide fluid communication between the lumen 12 and an external environment. A luer fitting 48 may be placed at the first end 16 of the elongated member. The luer fitting provides an entry point for the physician to deliver a fluid into the lumen 12 of the elongated member 14. A second luer fitting (not shown) may optionally be placed at the second end 18 of the elongated member 14, thus allowing the fluid to be delivered into the lumen 12 at one or both ends 16, 18 of the elongated member 14 as desired. While this example uses a luer fitting 48, any fluid connection fitting well known in the art may be placed at the ends 16, 18, or any other part, of the elongated member 14 to provide an entry point into the lumen 12.

Figure 2:
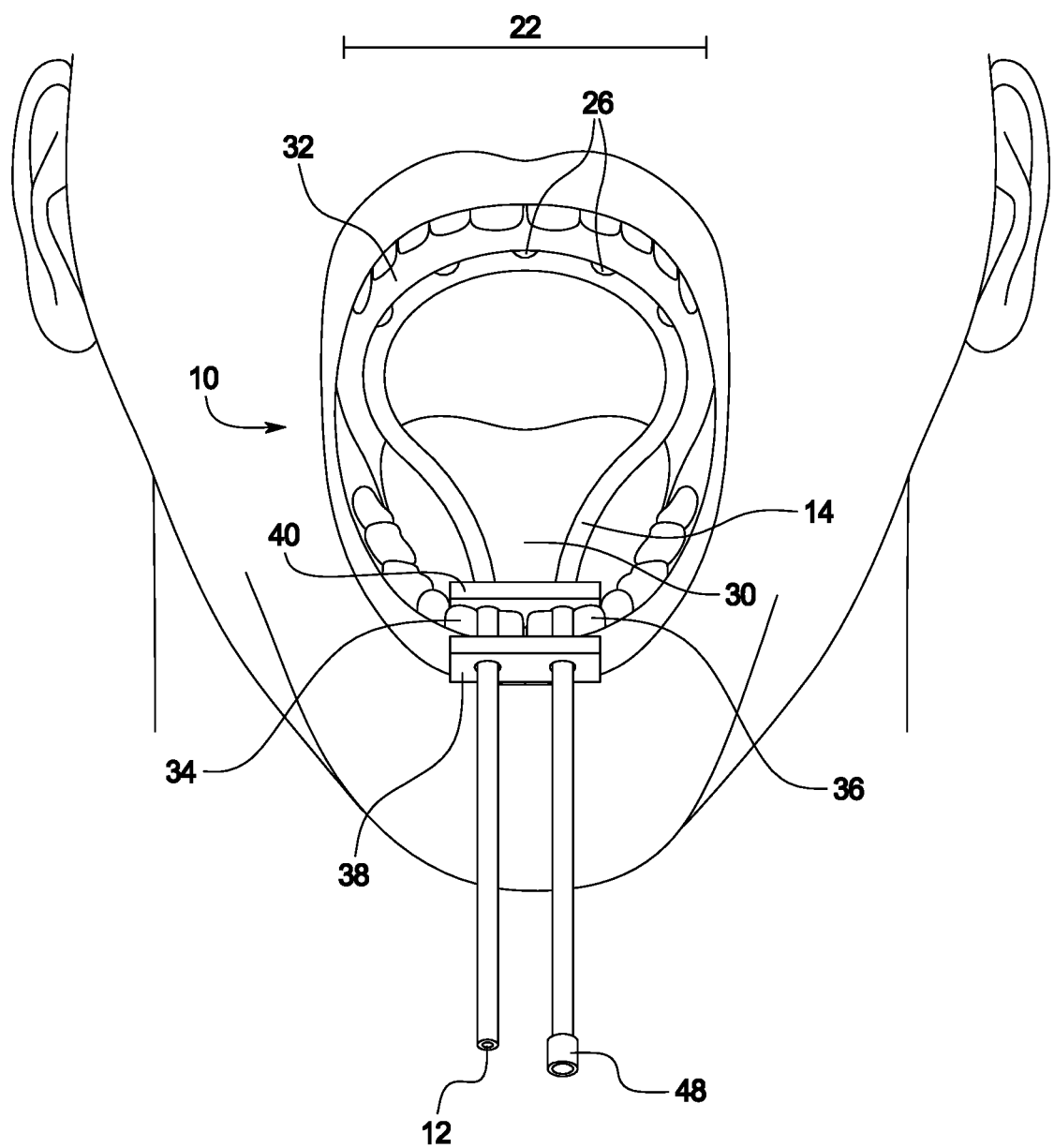
FIG. 2 is a drawing of a fluid delivery system inserted into a patient's mouth.
Figure 3:
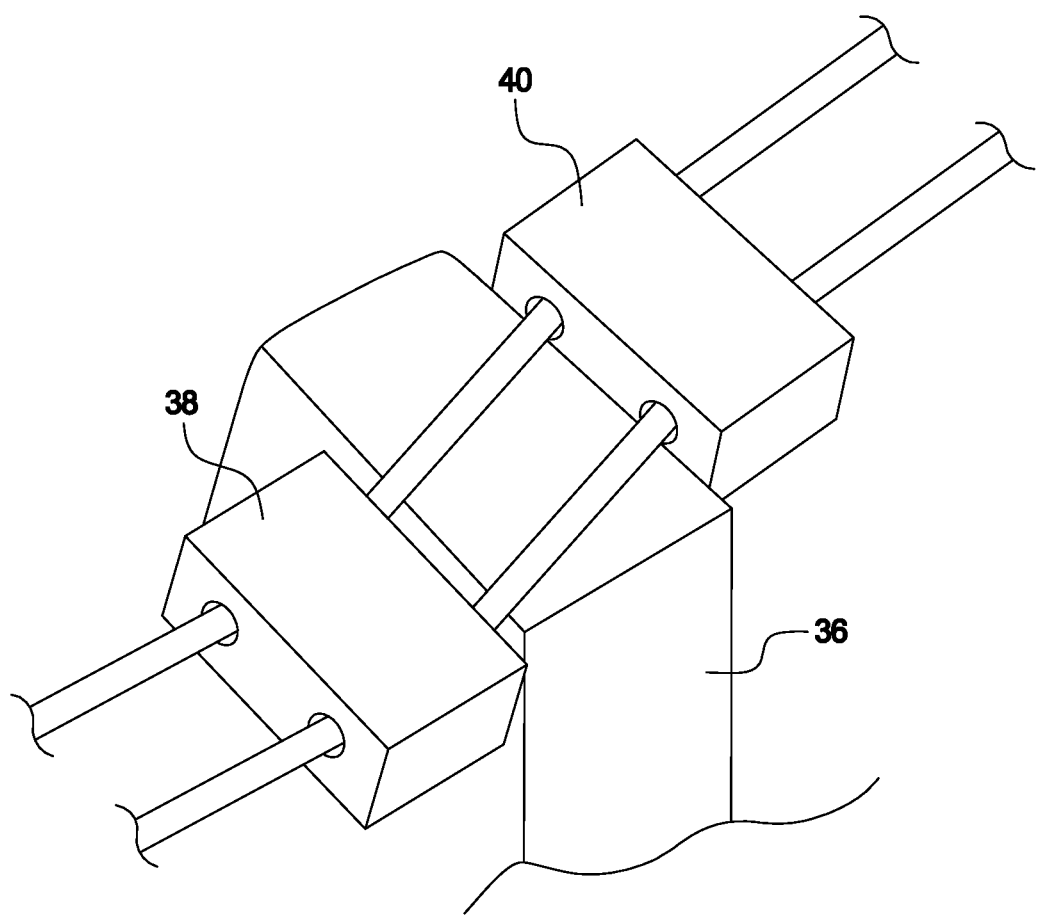
FIG. 3 is a detailed view of a locking system used in combination with the fluid delivery system.

FIG. 2 shows the fluid delivery system 10 inserted into a patient's mouth 30. The central portion 22, along with portions of the first and third portions 20, 24, may be inserted into the patient's mouth 30 such that the central portion 22 is positioned near or contacts the posterior wall 32 of the mouth 30. The fluid delivery system 10 may include a locking system 34 that interacts with the patient's teeth 36. The locking system 34 can be adjustable to different sized mouths and then locked into place to secure the fluid delivery system 10 within the patient's mouth 30. In this embodiment, the locking system 34 includes a first block 38 that is configured to engage the outside of the patient's teeth 36 and second block 40 that is configured to engage the inside of the patient's teeth 36. FIG. 3 shows a detailed view of the locking system's interaction with the patient's teeth 36. Both blocks 38, 40 may be slidably engaged with the first and third portions 20, 24. The blocks 38, 40 may be locked on the elongated member 14 once they, along with the rest of the fluid delivery system 10, have been properly positioned for the patient's mouth 30, thus preventing, or at least limiting, movement of the fluid delivery system 10 with respect to the patient's mouth 30. The blocks 38, 40 may be locked (and thus prevent slidable movement with respect to the elongated member 14) to the elongated member 14 using a variety of locking devices, including but not limited to: hinged lids and cord locks. The locking system 34 can be designed to engage with the bottom, top, or both rows of teeth 36. Alternatively, the locking system 34 may engage with another feature of the patient's mouth 30 or the locking system 34 may not engage with any feature of the patient's mouth 30. While the present embodiment includes two blocks 38, 40 as part of the locking system 34, a variety of other designs are contemplated, including using a block on only one side of the teeth 36 (inside or outside the teeth 36), or separate blocks that are individually slidable along either the first or third portions 20, 24 of the elongated member 14. For example, a single block may be used that engages with the inside of the patient's teeth 36, which forces the central portion 22 to spread out along the interior of the patient's mouth 30, while preventing the fluid delivery system 10 from falling out of the patient's mouth 30. Once the fluid delivery system 10 is positioned in the mouth 30, a fluid, such as an anesthetic or nerve block, may be passed through the lumen 12 of the elongated member 14 and towards the ports 26. The fluid may then flow through the ports 26 into the patient's mouth 30 and down towards the patient's throat.

Figure 4:
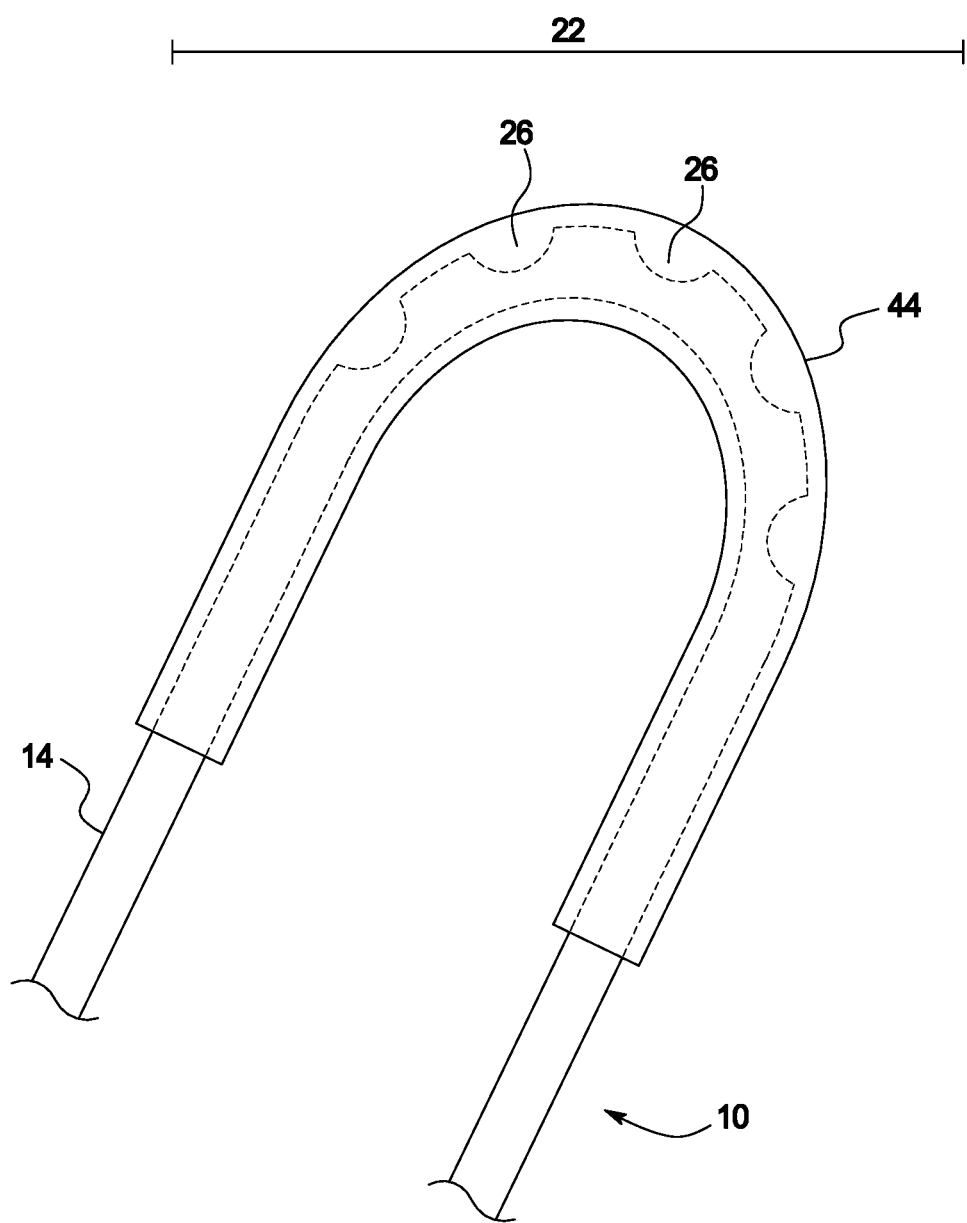
FIG. 4 is a detailed view of one portion of the fluid delivery system with a permeable membrane.

While the fluid delivery system 10 discussed above uses ports 26 to deliver the anesthetic or other fluid from the lumen 12 to the target site, other structures capable of permitting fluid drainage from within the lumen 12 to the target site may be used. For example, the central portion 22 may be made with a permeable membrane or other porous material that allows fluid to pass through the material at a controllable rate while the rest of the elongated member 14 is made with a non-porous material. Alternatively, as shown in FIG. 4, a permeable membrane 44 may be wrapped around the central portion 22 and ports 26 in the central portion 22 or provided as a tube with a lumen that is passed over the outside of the central portion 22. The permeable membrane 44 may be secured to the central portion 22 of the elongated member 14 with a variety of methods well known in the art including, but not limited to: shrink wrapping, adhesives, bonding. Alternatively, friction alone may be sufficient to maintain a connection between the permeable membrane 44 and the central portion 22, especially when the permeable membrane is provided as a tube. The permeable membrane 44 may provide further control to the flow rate of the fluid flowing into the patient's airway, since using the ports 26 alone may cause an undesirably high flow rate. However, the ports 26 may also be altered to control the flow rate of the anesthetic or other fluid from the lumen 12 to the target site. For example, the central portion 22 may include more ports 26 or the ports 26 may be larger in size to increase the flow rate. Conversely, the number of ports 26 may be decreased or the size of each port 26 may be decreased to decrease the flow rate. Similarly, the material properties of the permeable membrane 44 may be altered to decrease or increase the fluid flow rate as desired.

The ports 26 or permeable membrane 44 may be further modified to provide a uniform or non-uniform application of the anesthesia or other fluid into the patient's airway. For example, it may be desirable to have a higher flow rate near the midpoint of the central portion 22 while maintaining a lower flow rate near the ends of the central portion 22. To achieve a non-uniform flow rate, some ports 26 may be larger in size to permit more fluid to flow through those in comparison to other ports 26 that are smaller in size. Similarly, the permeable membrane 44 may be designed with varying material properties at different points in the membrane 44, thus allowing the flow rate to be non-uniform along the membrane 44.

Figure 5:
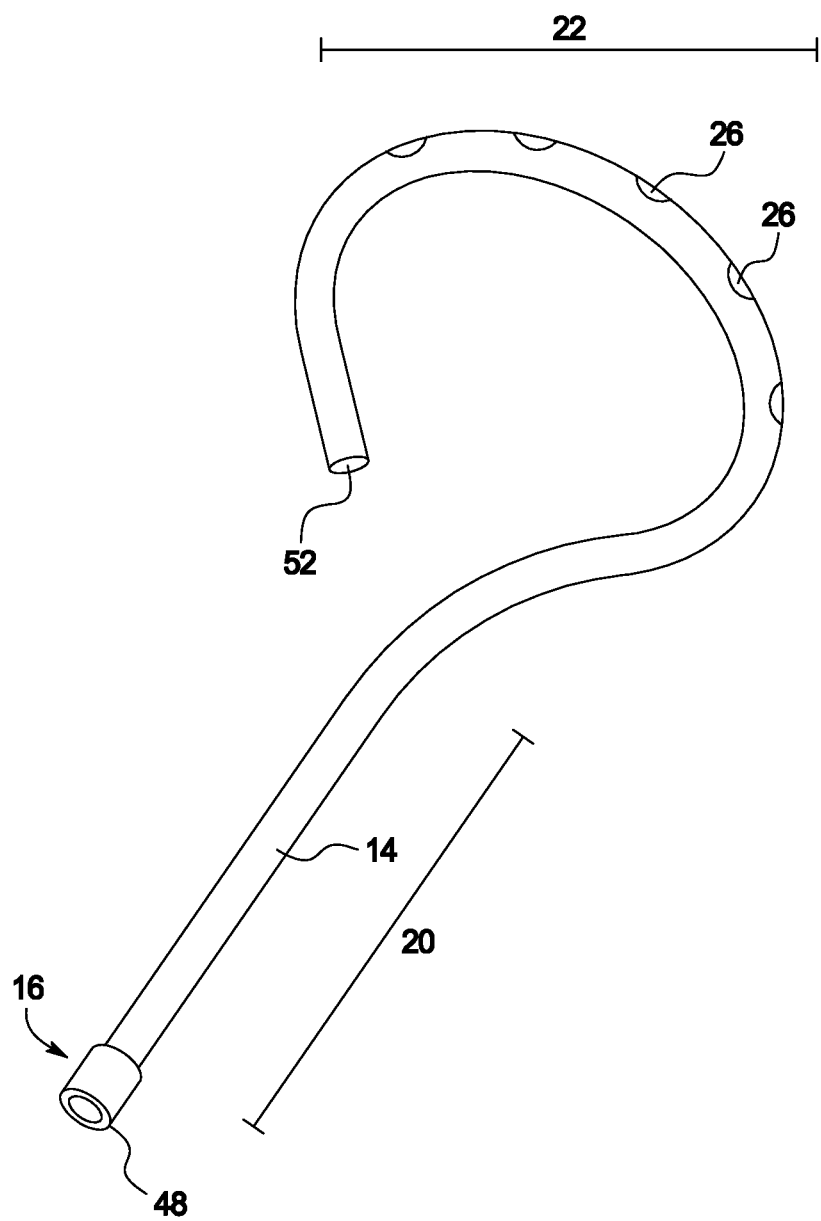
FIG. 5 is an alternate embodiment of a fluid delivery system.

The lumen 12 does not need to travel the entire length of the elongated member 14. In fact, it may be ideal for the lumen to extend only as far as necessary for the fluid to reach the ports 26. For this reason, a stop 50 may be placed in the lumen 12 in the central portion 22 of the elongated member 14, or at any other point along the elongated member 14 as desired. The stop 50 prevents the fluid from, in this instance, traveling into the third portion 24 of the elongated member 14. Thus, the fluid may be delivered into the lumen 12 at or near the first end 16 of the elongated member 14, travel through the first portion 20, into the central portion 22, and through the ports 26. The stop 50 prevents the fluid from unnecessarily traveling into the third portion 24. Alternatively, in another embodiment of the invention, the third portion 24 may be omitted entirely as shown in FIG. 5. The second end 52 of the elongated member 14 may be sealed so as to prevent any fluid from leaking out of the second end 52. Alternatively, the second end 52 may remain open so as to provide an additional opening for the fluid to flow into the patient's airway.

Figure 6:
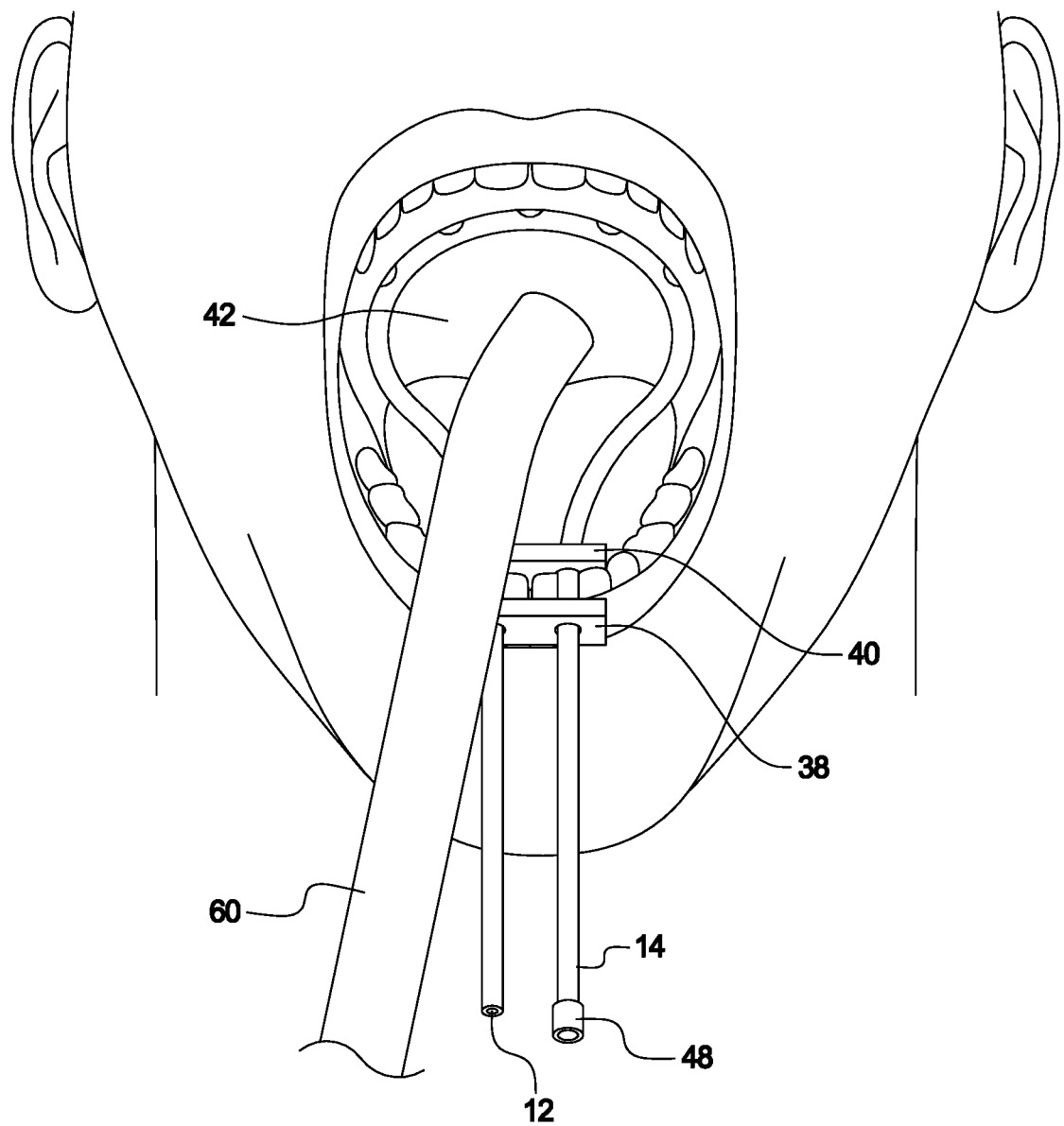
FIG. 6 is a drawing of a fluid delivery system used in combination with a tracheal tube.

While the embodiment described above includes a central portion 22 that has an arc-like shape and first and third portions 20, 24 that are uncurved in an axial direction, the shapes of these three portions 20, 22, 24 may vary. While a curved or arced shape for the central portion 22 may be preferable due to its conformance with the shape of the posterior wall 32 of the mouth 30, the central portion 22 may be designed in a variety of other shapes. Similarly, the first and third portions 20, 24 may be curved instead. However, the shape of the fluid delivery system 10 ideally allows an endotracheal tube 60 to be passed through an opening 42 in the fluid delivery system 10 and into the patient's trachea while maintaining the fluid delivery system 10 in position (FIG. 6). This feature allows anesthesia to be administered continuously or as needed for as long as the tracheal tube 60 is maintained in the patient.

The fluid delivery system 10 may be made with a variety of biocompatible materials. For example, the elongated member 14 may be made with silicone, polyurethane, nylon, and various other biocompatible materials. Ideally, the elongated member 14 is designed to be rigid enough to maintain its shape while in vivo while also being soft enough to prevent trauma to tissue. Additionally, the material for the elongated member 14 should be strong enough so as to prevent buckling or kinking thus maintaining the integrity of the lumen 12. The permeable membrane or porous material used to control the flow rate of the fluid can be made of, but is not limited to, a cellulose sponge or various porous plastic or porous fiber materials such as polypropylene, ethyl vinyl acetate, polyethylene, and polyester. As discussed above, the material properties of the permeable membrane may be altered to control the flow rate of the fluid from the lumen 12 into the patient's airway. The locking system 34 and blocks 38, 40 may be made of nylon, polyethylene, acetal, polyethylene terephthalate, and various other biocompatible materials.

In use, the fluid delivery system 10 may be inserted into the patient's mouth before or after the tracheal tube 60 has been inserted into the patient. If the tracheal tube 60 is inserted prior to insertion of the fluid delivery system 10, the embodiment shown in FIG. 7 may be snaked around the tracheal tube into the desired position. The other embodiments may be snaked around the tracheal tube 60 as well, but it may be more difficult to do so when compared to using the embodiment in FIG. 7. Preferably, the fluid delivery system 10 is inserted prior to insertion of the tracheal tube, as applying anesthetic through the fluid delivery system 10 will make insertion of the tracheal tube easier for both the physician and patient. The central portion 22 of the elongated member may be placed entirely within the patient's mouth 30. Then, the locking system 34 may be adjusted as necessary along the length of the elongated member 14 to fit the particular size of the patient's mouth 30. Once properly positioned, the locking system 34 may be secured in place such as by engaging with the patient's teeth 36. Once the fluid delivery system 10 has been properly positioned and secured, a fluid may be delivered into the lumen 12. The fluid may then travel along the lumen 12 towards the ports 26, where the fluid may flow from the lumen 12, through the ports 26, and into the patient's airway. The fluid may continuously flow through the lumen 12 for a specified period of time, or may be stopped and started as needed. Further, the flow rate may be adjusted as desired by increasing or decreasing the amount of fluid delivered to the lumen 12.

While the embodiments illustrated above are described in reference to use with an endotracheal tube, the device or similar devices may be used in a variety of other applications where it may be desirable to continuously provide a local anesthetic to the mouth, nose, upper airway, or gastrointestinal tract. For example, the device may be used with a gastrointestinal feeding tube. Additionally, the embodiments may be used to supply fluids other than anesthetic.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A fluid delivery system, comprising:
an elongated member comprising a lumen, the elongated member comprising a first portion, a second portion, and a third portion, the second portion disposed between the first portion and the third portion, wherein the elongated member is insertable into a patient's mouth such that the second portion is adapted to be disposed entirely within the patient's mouth while the first portion and third portion are adapted to extend from a point inside the patient's mouth to a point external the patient's mouth; and
a locking system engaged with the elongated member, the locking system configured to removably engage with the patient's teeth;
wherein the second portion is configured to allow drainage of a fluid from within the lumen to a point external the elongated member, and wherein the lumen comprises a stop positioned near a transition region between the second portion and the third portion, the stop preventing fluid communication during operation between a portion of the lumen within the second portion and a portion of the lumen within the third portion, and the fluid delivery system further comprising an opening through which a tracheal tube can be inserted.

2. The fluid delivery system of claim 1, further comprising:

a fluid connection fitting attached to a first end of the elongated member, wherein the fluid connection fitting is in fluid communication with the lumen.

3. The fluid delivery system of claim 1, wherein:

the locking system comprises a first block and a second block, the first block removably engageable with a front of the patient's teeth and the second block removably engageable with a back of the patient's teeth.

4. The fluid delivery system of claim 3, wherein:

the first and second blocks are each slidable along the first and third portions of the elongated member, wherein the first and second blocks are lockable to prevent sliding along the first and third portions of the elongated member.

5. The fluid delivery system of claim 1, wherein:

the second portion comprises at least one port that allows drainage of a fluid from within the lumen to a point external the elongated member.

6. The fluid delivery system of claim 5, further comprising:

a permeable membrane secured to an external surface of the second portion of the elongated member.

7. The fluid delivery system of claim 6, wherein:

the locking system comprises a first block and a second block, the first block removably engageable with a front of the patient's teeth and the second block removably engageable with a back of the patient's teeth;

the first and second blocks are each slidable along the first and third portions of the elongated member, wherein the first and second blocks are lockable to prevent sliding along the first and third portions of the elongated member.

8. The fluid delivery system of claim 1, wherein:

the second portion comprises an arced shape and the first and third portions are substantially straight along an axial direction.

9. A method of delivering a fluid, comprising:

providing a fluid delivery system, the fluid delivery system comprising an elongated member comprising a lumen, the elongated member comprising a first portion, a second portion, and a third portion, the fluid delivery system further comprising a locking system slidably engaged with the elongated member, wherein the second portion of the fluid delivery system is configured to allow drainage of a fluid from within the lumen to a point external the elongated member;

inserting the fluid delivery system into a patient's mouth such that the second portion is disposed entirely within the patient's mouth and the first and third portions extend at least partially into the patient's mouth;

engaging the locking system with the patient's teeth;

supplying a fluid through the lumen of the fluid delivery system such that the fluid flows out of a portion of the lumen disposed within the second portion of the elongated member and into the patient's body; and inserting a medical instrument through an opening in the fluid delivery system and into the patient's trachea.

10. The method of claim 9, wherein:

the locking system further comprises a first block and a second block, wherein the first block is engageable with a front side of the patient's teeth and the second block is engageable with a back side of the patient's teeth.

11. The method of claim 10, wherein:

the step of engaging the locking system with the patient's teeth further comprises sliding the first block along the elongated member until it is adjacent to the front side of the patient's teeth, locking the first block to the elongated member so as to prevent movement of the first block with respect to the elongated member, sliding the second block along the elongated member until it is adjacent to the back side of the patient's teeth, and locking the first block to the elongated member so as to prevent movement of the first block with respect to the elongated member.

12. The method of claim 9, wherein the medical instrument is a tracheal tube.

* * * * *